United States Patent [19]
Mersch

[11] Patent Number: 5,408,998
[45] Date of Patent: Apr. 25, 1995

[54] VIDEO BASED TISSUE OXIMETRY

[75] Inventor: Steven H. Mersch, Germantown, Ohio

[73] Assignee: Ethicon Endo-Surgery, Cincinnati, Ohio

[21] Appl. No.: 209,666

[22] Filed: Mar. 10, 1994

[51] Int. Cl.⁶ ............................................. A61B 5/00
[52] U.S. Cl. .................................... 128/633; 128/634; 128/665
[58] Field of Search ............................ 128/633–634, 128/664–667; 356/39–41

[56] References Cited

U.S. PATENT DOCUMENTS

| | | | |
|---|---|---|---|
| Re. 33,643 | 7/1991 | Isaacson et al. | 128/633 |
| 3,638,640 | 2/1972 | Shaw | 128/663 |
| 4,353,792 | 10/1974 | Lubbers et al. | 128/634 |
| 4,407,290 | 10/1983 | Wilber | 128/633 |
| 4,819,752 | 4/1989 | Zelin | 128/633 |
| 4,953,539 | 9/1990 | Nakamura et al. | 128/633 |
| 4,998,973 | 3/1991 | Kikuchi | 128/634 X |
| 5,078,150 | 1/1992 | Hara et al. | 128/634 X |

*Primary Examiner*—Angela D. Sykes
*Attorney, Agent, or Firm*—Susan M. Schmitt

[57] ABSTRACT

A video oximetry device and method is provided in which an endoscopic device is used to obtain and determine oxygen saturation levels at a tissue site. A video image illustrating blood oxygen saturation and/or tissue perfusion is derived and displayed.

31 Claims, 2 Drawing Sheets

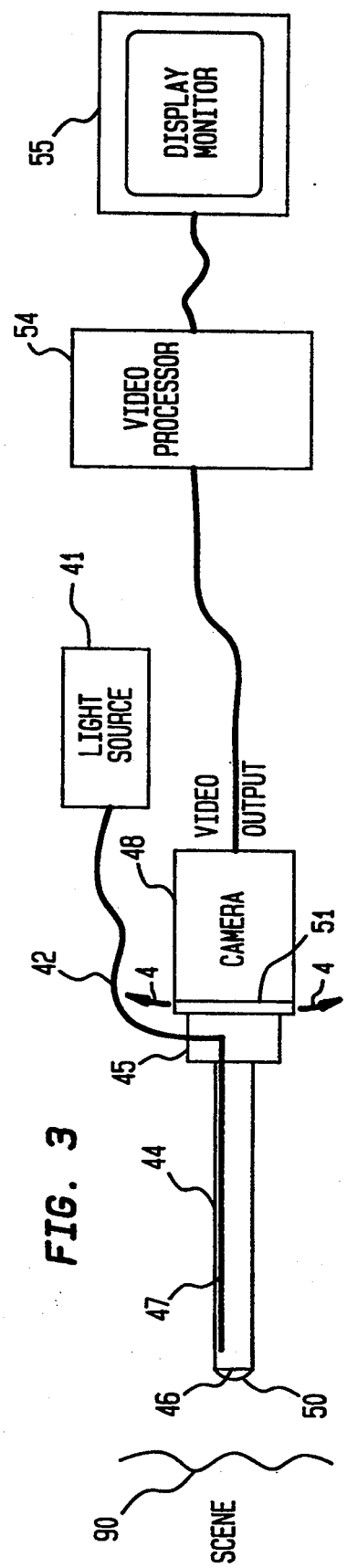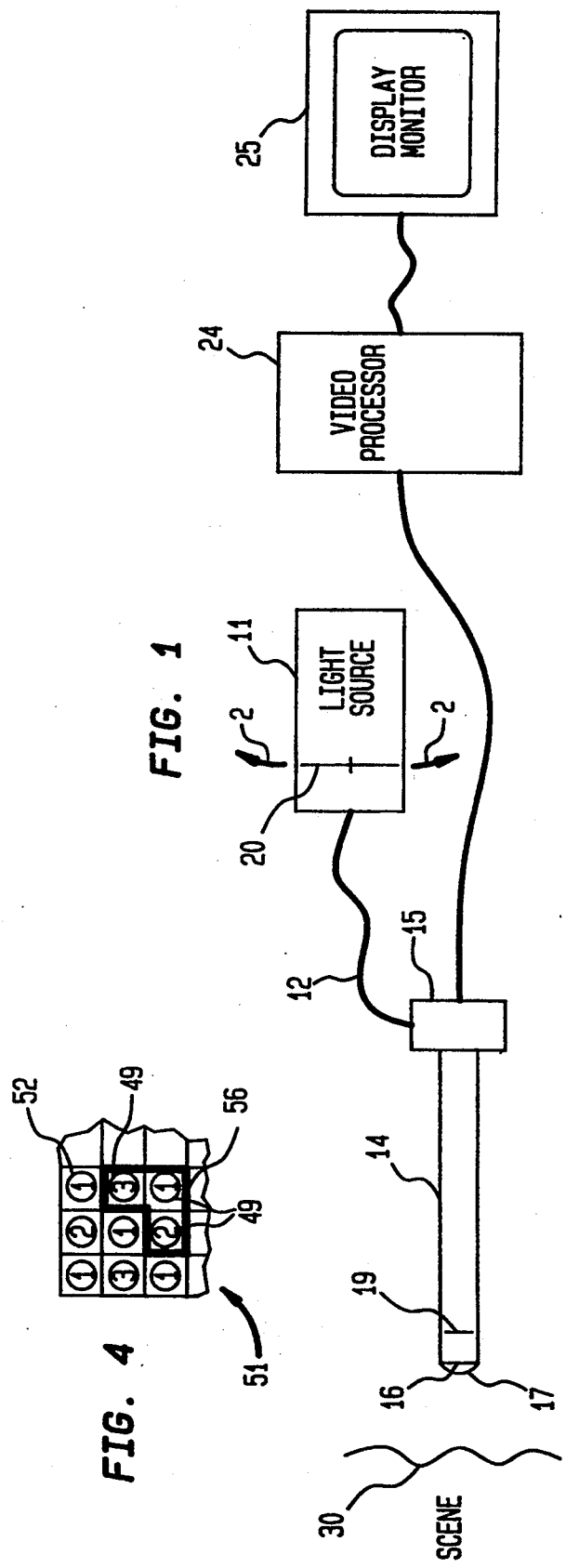

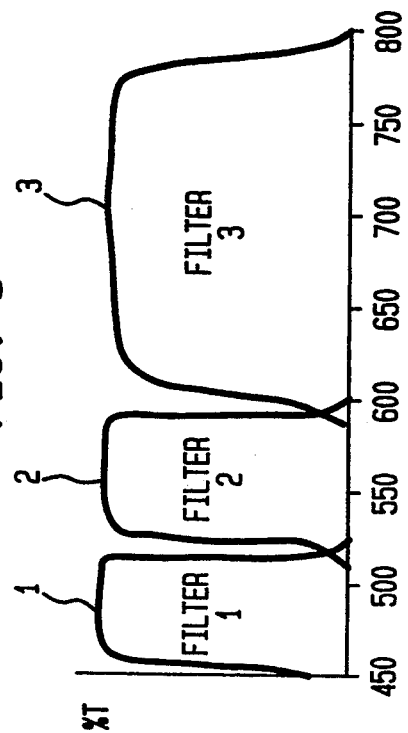
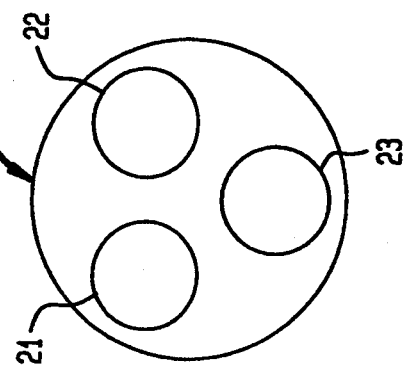
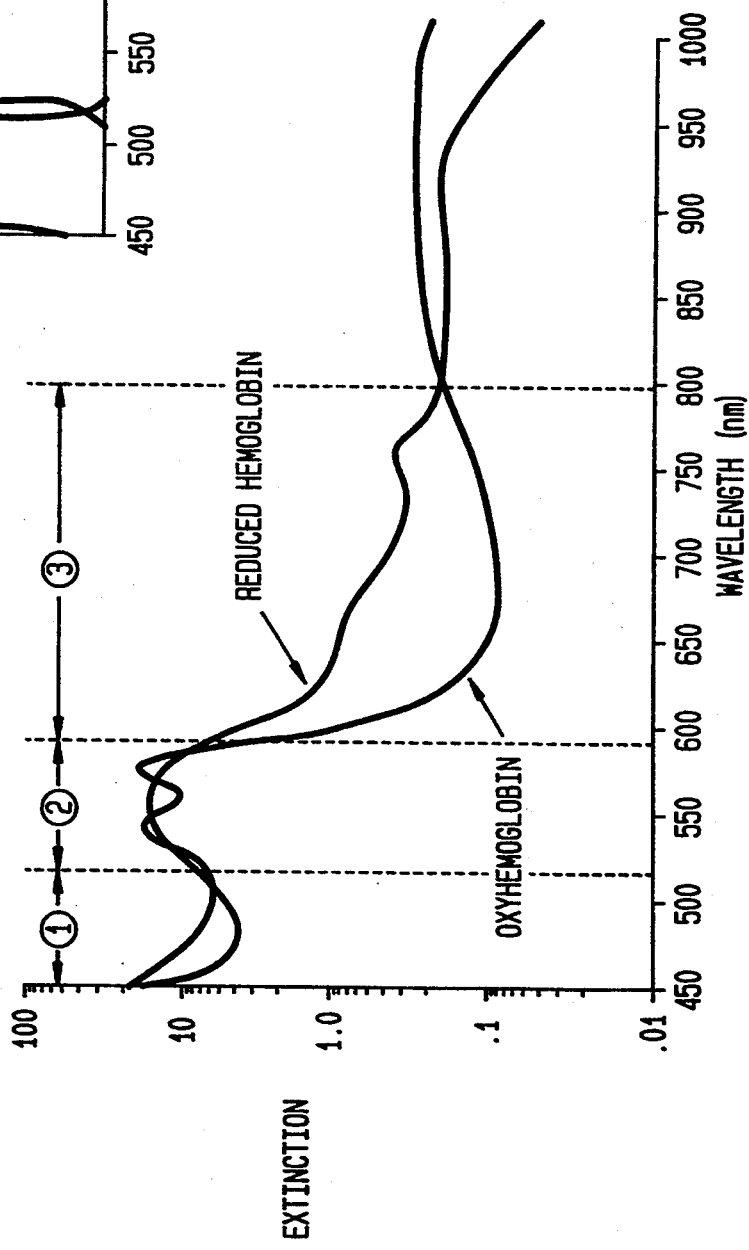

VIDEO BASED TISSUE OXIMETRY

FIELD OF THE INVENTION

This invention relates to an endoscopic device and method for determining and illustrating through a video image, blood oxygen saturation levels and/or tissue perfusion.

BACKGROUND OF THE INVENTION

Oximetry has been used for non-invasive monitoring of blood and tissue oxygen saturation levels using devices such as finger tip pulse oximeters. Pulse oximeters determine a patient's arterial blood oxygen saturation levels, which is particularly useful in monitoring patients while under anesthesia. Typically, a finger tip oximeter transmits a light from an LED through the finger tip to a photoreceptor opposite the LED which detects the absorption of predetermined wavelengths of light. Because the light absorption for oxygenated and reduced hemoglobin are different, the absorption level may be used to determine oxygen saturation levels. Light reflectance has also been used to determine oxygen saturation levels. The term light includes the entire electromagnetic radiation range and specifically includes the ranges of light used to determine blood oxygen concentration. Various methods of measuring oxygen saturation levels using pulse oximetry are known in the art. Some of these methods are described, for example in U.S. Pat. Nos. 4,759,369 and 4,807,631.

Oximetry is based on the principle that the color of blood is a function of saturation of hemoglobin with oxygen. The absorption or reflectance of light is different for oxygen saturated hemoglobin (oxyhemoglobin) and reduced hemoglobin. The absorption or reflectance also varies for each depending on the wavelengths of light directed toward the blood or tissue. The differences in light absorption (measured as light transmission or reflection) between reduced and oxyhemoglobin as related to wavelength can be described by the molecular extinction coefficients of hemoglobin for each wavelength. Using the hemoglobin extinction curves based on the absorption or conversely reflectance of light directed toward vascularized tissue or organs, oxygen saturation can be calculated from a ratio derived from an absorption formula known as Beer's Law. These relationships are well known in the art and are routinely used in one form or another to determine oxygen saturation levels in blood or tissue.

Typically, two or more wavelengths of light are used to illuminate tissue. The degree of absorption of light is determined by either measuring the amount of light transmitted through the tissue or the amount of light backscattered from the tissue. The term backscattered is meant herein to be diffuse as opposed to specular reflection. The amount of light reflected is measured using photodiodes which convert the light to a corresponding signal. The signal is normalized and processed using known signal processing techniques based on Beer's Law, to eliminate variables in the signal due to varying skin pigmentation, thickness of skin, perfusion, patient motion, etc. Thus, for example, in pulse oximetry, the normalized signal represents the pulsed waveform caused by the pulsing of the arterial blood. The pulsed signal is used in calculating arterial oxygen saturation. Because the detected pulsatile waveform is produced solely from arterial blood, using the amplitude at each wavelength and Beer's law allows exact beat to beat continuous calculation of arterial hemoglobin oxygen saturation with minimal interference from surrounding venous blood, skin, connective tissue or bone. The resulting information is used to calculate arterial blood oxygen saturation.

Oximetry has also been described for determining either organ or tissue oxygen consumption. In one method, the metabolic rate of an internal body organ or tissue is determined by blocking the blood supply to the organ or tissue. Using similar light reflectance or absorbance techniques, oxygen saturation levels are measured over a period of time and are used to determine tissue oxygen consumption as a function of time. An example of such methods and devices may be found in U.S. Pat. Nos. 4,463,762 and 4,513,751.

SUMMARY OF THE INVENTION

It is an object of the present invention to provide a device and method for use in endoscopic surgery to determine blood and/or tissue oxygen saturation levels. The term "endoscopic" as used herein is meant to refer to any surgical procedure using either natural body openings and/or small artificial openings made by puncture or incision. An endoscope as used herein is meant to be a viewing device for use in endoscopic procedures.

It is another object of the invention to endoscopically provide a perfusion image which will indicate tissue oxygen perfusion for an endoscopically imaged area. It is a further object to provide a video image on which a map of values corresponding to oxygen saturation levels can be indicated using a colored or shaded map superimposed on an endoscopically imaged area of tissue.

A first embodiment of the present invention provides an endoscope with a light source, optical filters for filtering light of predetermined wavelengths, located at the light source, an imaging means (e.g., a lens), and, an array of light sensors such as a light sensitive charge coupled device located at the distal end of the endoscope.

The color filter cycles through an alternating pattern at a given frequency, filtering light at the light source, and causing emission of a repeating series of corresponding light components at the distal end of the endoscope. Each light component is comprised of a given wavelength or band of wavelengths filtered by a corresponding filter at the light source.

In one embodiment, for example, the light source is strobed at a frequency of 180 hz. Light is filtered at three distinct intervals to emit light of three corresponding bands of wavelengths from the distal end of the endoscope, each band of wavelengths thus being cycled at 60 hz.

A receptor located at the distal end of the endoscope comprised of array of sensors, (e.g., a CCD) detects the backscattered light reflected back through the imaging means to the distal end of the endoscope at each of the three intervals, i.e., for each of the three components emitted.

The images of light detected by the array of sensors are processed on a pixel by pixel basis using known image processing and oximetry techniques. The reflected light for each of the three components corresponding to the particular pixel are used to calculate oxygen saturation levels for the given pixel. A pixel map of oximetry values is thereby produced. The pixel map is cycled at 60 hz after a cycle of three components of emitted light is completed.

In another embodiment the device comprises an endoscope with a light source, a camera, an array of sensors, and a color filter located at the sensor array. The sensor array and filter are located at the distal end of the camera. The filter comprises an array of filters of three different wavelengths or bandwidths of wavelengths. Each filter of the array corresponds to one pixel or a subset area of pixels of the entire pixel array. The three bandwidth filters alternate so that a subset area of filters contains representative information for each light component for a subset area of a video image. Light is directed toward tissue and light is reflected back through the scope to the filters and photosensors at the camera's distal end. The light is filtered then detected by the photodetectors. The intensity of light for each subset area of pixels and filters is processed. Information comprising light from the three bandwidths is used to determine blood and/or tissue oxygen levels.

The resulting signals of either embodiment described above may be sent to a video processor which forms an image based on the output signals from the endoscope for each pixel. The image may be displayed on a display monitor using image enhancement to illustrate tissue oxygen saturation levels. The techniques used to enhance the image may vary depending on what information is of interest to the user. For example, the map of values may be falsely colored, for example, with red being the most oxygenated and blue being the least oxygenated. The false colored image could be overlaid on a regular black and white endoscope image for the same area of tissue, thereby presenting to the surgeon a perfusion or oximetry image or area map which spatially corresponds to the same area of tissue.

In a preferred embodiment, a glare elimination filter is added to the endoscope to improve the accuracy of the oximeter by ensuring that only light backscattering from the volume of the tissue is analyzed and confounding reflections from the surface of the tissue are eliminated. Internal organs, for example, reflect light and produce glare due to their wet, glossy surfaces. One type of reflection termed "diffuse" is a scattered reflection from the surface or subsurface of the illuminated object and contains the desirable information for purposes of determining oxygen saturation levels of tissue or blood. A second type of reflection is what is known as mirrored reflection or "specular" reflection and does not change the incident or illuminating light. This reflection confounds the oximetry information. Therefore the present invention provides a device and method for determining blood and/or tissue oxygen concentration levels using an endoscope which corrects for undesirable glare reflecting from the tissue. According to this embodiment, a first polarizing filter is provided at the distal end of an illumination means of the endoscope. Light used to illuminate a tissue scene is first passed through this filter. The light reflected from the tissue scene is passed through a second polarizing filter at a different polarizing angle, most preferably at 90 degrees, from the first polarizing filter.

The image may be used for real-time determination of blood perfusion of tissue and changes in blood perfusion. The image may be used to determine and display arterial blood saturation levels. The image may also be used to show metabolism of tissue or organs or the change in such metabolism.

DETAILED DESCRIPTION OF THE DRAWINGS

FIG. 1 illustrates a block diagram of the video oximeter of the present invention;

FIG. 2 illustrates a cross section of FIG. 1 through the lines 2—2;

FIG. 3 illustrates a block diagram of a second embodiment of the video oximeter of the present invention;

FIG. 4 illustrates a cutaway partial cross section of FIG. 3 through the lines 4—4;

FIG. 5 illustrates hemoglobin extinction curves for oxyhemoglobin and reduced hemoglobin; and FIG. 6 illustrates three bandwidths of light used in the preferred embodiment of the present invention.

DETAILED DESCRIPTION OF THE PREFERRED EMBODIMENT

Referring to FIG. 1 a first embodiment of the present invention provides an endoscope 14, a light source 11, an optical filter wheel 20 for filtering of light of predetermined wavelengths located at the light source 11, a charge coupled device (CCD) 19 located at the distal end 16 of the endoscope 14, and a lens 17 for directing the light towards a scene 30. Preferably the light source is a white light source.

The optical filter wheel 20 comprises three filters 21, 22, and 23 corresponding to three light components 1, 2, and 3 (FIG. 5). Each light component corresponds to a particular wavelength or band of wavelengths of light. The light source 11 is strobed at a given frequency, causing light to be transmitted through optical fibers 12 which extend to the distal end 16 of the endoscope 14. The light is emitted from the fibers 12 and focused with the lens 17 towards the scene 30 which is comprised of blood perfused tissue. The filters 21, 22, and 23 cycle through an alternating pattern at a frequency of 180 hz, filtering light of the light source, and causing emission of a repeating series of corresponding light components 1, 2, and 3 at the distal end 16 of the endoscope 14. Each light component 1, 2, and 3 corresponds to a band of wavelengths described below and is filtered at one of three distinct intervals, each light component or band of wavelengths thus being cycled at 60 hz.

The CCD 19 comprises an array of sensors which detects and images the intensity of the light backscattered to the distal end of the endoscope at each of the three intervals, i.e., for each of the three components 1, 2, and 3, emitted. The CCD 19 provides an array of electrical signals corresponding to the light reflected back from the tissue. The electrical signals are communicated to a video processor 24. The video processor 24 processes and enhances the signal and determines oxygen saturation levels, on a pixel by pixel basis. The video processor provides the resulting information to a display monitor 25 to be displayed.

An example of a scope which may be used is, an Olympus Model EVIS200 endoscope.

Referring now to FIG. 2 there is illustrated another embodiment of a video oximeter of the present invention. A light source 41 sends light through light fibers 42 to the distal end 46 of an endoscope 44. The light fibers 42 at the distal end 46 of the endoscope 44 direct the light at a scene 90 comprised of blood perfused tissue.

A camera 48 is coupled to the proximal end 45 of the scope 44. A filter 51 is inserted at the distal end of the camera. An array of light sensors 49 is located at the distal end of the camera 48 proximal to the filter 51. The filter 51 is comprised of an array of pixel filters 52, each associated with a corresponding light sensor 49.

Light is backscattered through the relay lens 50 at the distal end 46. The backscattered light is transmitted to the camera 48 through a series of rod relay lenses 47 extending from the distal end 46 to the proximal end 45 of the scope 44. The relay lenses 47 focus the backscattered light from the tissue to an image at the proximal end 45.

The light is passed through the filter 51 and sensed by the light sensors 49. Each pixel filter 52 filters one of three light components 1, 2, or 3. Each light component corresponds to a predetermined light wavelength or bandwidth of wavelengths. The filtered light from each pixel filter 52 is then detected by a corresponding one of the light sensors 49. Each of the light sensors 49 convert the light energy into an electrical signal corresponding to the intensity of light received by the sensor. Each subset 56 of filters 52 and corresponding light sensors 49 corresponds to 1 pixel of information. Thus, for each light sensor 49 there is an electrical signal relative to the amount of light of a particular bandwidth reflected from an area of the tissue 90.

The light components 1, 2, and 3 (FIG. 3) are arranged in an alternating fashion on the array 51 so that a subset area 56 of filters 52 contains representative information for each of the three light components 1, 2, and 3. The subsets 56 may be overlapping or may represent numerous configurations of filters on the array. A variety of patterns of filter subsets are established for color CCD cameras. Any one of these patterns may be use for image processing depending on what information is of interest. The array of information is communicated to a video processor 54 which processes the input signal using known signal processing techniques and displays a resulting image on a display monitor 55.

The resulting signal of either the first or second embodiment described above is sent to a video processor 24 or 54, respectively, which forms an image based on the output signal from the CCD 19 or the array of sensors 51, respectively. The image may be displayed on a display monitor using image enhancement to illustrate tissue oxygen saturation levels.

In a preferred embodiment, a glare elimination filter (not shown) is added to the endoscope to improve the accuracy of the oximetry data by helping insure that only light backscattering from the volume of the tissue is analyzed and confounding reflections from the surface of the tissue are eliminated. A glare elimination device is intended to virtually eliminate the specular light reflected back to the endoscope.

In a preferred embodiment backscattering oximetry is used. Backscattering oximetry is described in Donahoe, T. M., and Longini, R. L. "A New Non-invasive Backscattering Oximeter" IEEE Seventh Annual Conference of the Engineering in Medicine and Biology Society, p. 144–147 (1985). Backscattering oximetry involves the measurement of light that is scattered back from the surface of the tissue. Backscattering oximetry is based on the application of photon diffusion theory. The spectral light which is reflected from the surface does not contain information relating to the absorption of light by tissue or blood. If the spectral light is filtered, the remaining light is the light diffused from the tissue. The diffused light is the backscattered light from which oximetry determinations can be made. Both the light source and light sensors are positioned on the same tissue surface. Both light absorption and light scattering are analyzed.

FIG. 5 illustrates three bands of wavelengths selected for use in the present invention. FIG. 6 illustrates the hemoglobin extinction curves for oxygenated and reduced hemoglobin at the bands of wavelengths illustrated in FIG. 5. Many variations of wavelengths may be selected to determine blood or tissue oxygen levels as is well known in the art. Currently available finger tip oximeters, for example, use the 920 nm and 660 nm wavelengths.

Preferably the following criteria are met in selection of which wavelengths or bands of wavelengths are used:

1) an isobestic point should be used, i.e., a point or a band of wavelength where the extinction values or averaged values for oxyhemoglobin and reduced hemoglobin are equal; and 2) one or more wavelengths or bands of wavelengths for which the oxygenated and reduced hemoglobin show significantly different optic absorption should be used.

The wavelengths selected in the illustrated embodiment comprise light components of three bands of wavelengths, 1, 2, and 3. Component 1 is comprised of light wavelengths 450 nm–520 nm. Component 2 is comprised of 520 nm–590 nm. Component 3 is comprised of wavelengths 590 nm–800 nm. The average extinction value for oxygenated hemoglobin and reduced hemoglobin for component 2 is equal, thus representing an isobestic point. The average extinction value for reduced hemoglobin for component 1 is less than that of oxygenated hemoglobin. And, the average extinction value for reduced hemoglobin for component 3 is greater than that of oxygenated hemoglobin. Thus components 1 and 3 satisfy the second criterion above where one or more wavelengths for which the oxygenated and reduced hemoglobin show significantly different optical absorption. The isobestic point helps to normalize the data for different tissue types. Generally, any differences at the isobestic point can be attributed to factors other than differences in reduced and oxygenated hemoglobin levels since the extinction coefficients for each are the same at the isobestic point.

There are many video processing systems available and known in the art which would perform the data processing. This processing can be performed on a computer system including a personal computer. Because of movement at the scene during a heartbeat cycle, a correction for such motion is incorporated into the video processing system. Images from at least two points in time, preferably at the peak and valley of the heartbeat cycle, are compared to find common physical characteristic points. The images may then be overlaid and oximetry calculations made on a pixel by pixel basis. Frames of maximum and minimum value for each light component over one heartbeat cycle are identified. This will identify the peak and valley of the pulse. The frame at the maximum value is designated frame A and at the minimum value is designated frame B. Using software known in the art, correction is made for motion occurring during time between Frames A and B. A pixel by pixel oximetry determination is made for the overlaid images of Frames A and B. Algorithms which may be used to make the tissue oximetry determination are known in the art. A number is assigned to each to pixel location based on the resulting oximetry values. Each number corresponds to a color where the color indicates oxygen saturation level. For example, blue would indicate no oxygen saturation and red would indicate a maximum oxygen saturation level. Other colors could indicate levels in between. The resulting array of values is then presented as a false color video image. The image may also, for example, be overlaid on a black and white image of the scene. The oximetry image of the invention may be displayed in real time at a frequency of an integer fraction of the frequency of the interval on series of intervals required to obtain oxygen saturation values for the tissue image area.

This invention is described in connection with a specific embodiment of a video oximeter used to measure arterial oxygen saturation levels. Naturally the invention may be used to measure other tissue oxygen saturation values, for example, to determine rate of oxygen metabolism in organs or other tissue. Accordingly, it will be understood by those skilled in the art that various changes and modifications may be made in the invention without departing from its scope, which is defined by the following claims and their equivalents.

What is claimed is:

1. A method for generating a video oximetry signal comprising the steps of:
   using an endoscope to visualize a portion of tissue;
   providing a light source for illuminating the tissue and an array of light sensors for sensing light reflected from the tissue;
   illuminating the tissue during a series of time intervals, wherein during each said interval, said tissue is illuminated with a predetermined light component comprising at least one predetermined light frequency;
   using the array of sensors to sense the amount of light reflected by said tissue during each said interval, each said sensor sensing light reflected from a subset area of said illuminated tissue;
   converting said amount of light sensed by each said sensor to an electrical signal;
   processing said signals to provide a light intensity value for each said sensor corresponding to each said interval;
   using said intensity value for each said interval to calculate a tissue oxygen saturation value for each said subset area; and
   creating an area map from said oxygen saturation values for each sensor, wherein said area map spatially corresponds to said subset areas of said tissue.

2. The method of claim 1 further comprising filtering light during each said time interval to provide said corresponding predetermined light component for each said interval.

3. The method of claim 2 further comprising providing a plurality of optical filters located at the light source.

4. The method of claim 1 further comprising providing a video image of said area map, said video image comprised of a plurality of pixels, wherein each said subset area corresponds to at least one said pixel.

5. The method of claim 1 wherein said series of time intervals is repeated for a plurality of cycles.

6. The method of claim 3 wherein said cycles are repeated at a predetermined frequency.

7. The method of claim 1 further comprising:
   obtaining an image comprised of a plurality of pixels, wherein each said pixel corresponds to at least one of said subset areas of said tissue;
   assigning a color to each said oxygen saturation value of each said subset area, said color varying in frequency with said oxygen saturation values; and
   overlaying said color of each subset area on said corresponding pixel of said image to provide an oximetry image illustrating measured oxygen saturation values for each pixel.

8. The method of claim 7 further comprising providing a real time image of oxygen saturation values by repeating said time intervals for a plurality of cycles at a first predetermined frequency, wherein said real time image is cycled at a second frequency, said second frequency measured as an integer fraction of said first frequency.

9. The method of claim 1 further comprising:
   reducing the glare of reflected light from the tissue scene by providing a first polarizing filter between the light source and the tissue and a second polarizing filter between said tissue and said array of sensors; wherein said first filter is oriented at a different polarizing angle from the second filter.

10. The method of claim 9 wherein said plurality of filters is a filter wheel; and
    further comprising the step of rotating said filter wheel at a predetermined rate.

11. The method of claim 1 wherein said array of sensors is a charge coupled device.

12. The method of claim 1 further comprising:
    sending said electrical signals to a video processor to form an image from said electrical signals taken from each sensor, wherein said image is comprised of a plurality of pixels;
    processing and enhancing said electrical signals with a video processor to provide corresponding oxygen saturation levels for each said sensor on a pixel by pixel basis; and
    displaying the resulting information on a display monitor.

13. The method of claim 12 wherein said filter wheel includes at least three filters.

14. The method of claim 1 further comprising the step of providing said area map at the completion of said series of time intervals.

15. The method of claim 1 wherein said series of intervals comprises at least three intervals at which correspondingly is emitted at least three light components, each comprising a band of light wavelengths; and wherein said oxygen saturation values are calculated from light intensity values from each of said at least three intervals.

16. The method of claim 15 wherein:
    said at least three intervals comprises respectively a first, second and third light component;
    said first light component represents an isobestic point;
    said second light component represents a band of wavelengths where the average extinction values for oxyhemoglobin are greater than the average extinction values for reduced hemoglobin; and
    said third light component represents a band of wavelengths where the average extinction values for oxyhemoglobin are less than the average extinction values for reduced hemoglobin.

17. The method of claim 16 wherein:
    the first light component includes wavelengths of between about 520 nm and 590 nm;
    the second light component includes wavelengths of between about 450 nm and 520 nm; and the third light component includes wavelengths of between about 590 nm and 800 nm.

18. A method for generating a video signal comprising the steps of:
using an endoscope to visualize a portion of a tissue having an image area;
providing:
a) a light source for illuminating said tissue,
b) an array of light sensors associated with said endoscope;
c) a first optical filter located at the sensor array, said first optical filter comprised of a plurality of filters for a plurality of light components, wherein each said filter corresponds to a sensor of said array and wherein each said filter corresponds to a predetermined light component; and
d) a camera associated with the endoscope;
illuminating said tissue during at least one interval by directing light from the light source at the tissue;
filtering light reflected from said tissue;
using said sensors to sense the amount of filtered light reflected from the tissue;
providing at least one subset of said plurality of filters, each of at least one subset filters corresponding to a subset area of said tissue, and comprising at least one filter for each of said plurality of light components;
converting the amount of light sensed by each said sensor to an electrical signal;
processing the signals at said interval for each said sensor corresponding to a said subset area to calculate an oxygen saturation value of said subset area; and
creating an area map of oxygen saturation levels comprised of oxygen saturation values for each subset area, wherein said map spatially corresponds to said image area of said tissue.

19. The method of claim 18 further comprising filtering light during each said time interval to provide said corresponding predetermined light component for each said interval.

20. The method of claim 18 further comprising providing a series of rod relay lenses located between said camera and said tissue, wherein the emitted light is sensed after it returns through said relay lenses.

21. The method of claim 18 further comprising transmitting said light reflected by the scene from the distal end of the endoscope to the proximal end, wherein said filters and sensors are located at said proximal end of the endoscope.

22. The method of claim 18 further comprising:
obtaining an image comprised of a plurality of pixels, wherein each said pixel corresponds to at least one of said subset areas of said tissue;
assigning a color for each said oxygen saturation value of each said subset area said color varying in frequency with said oxygen saturation values; and
overlaying said color of each subset area on said corresponding pixel of said image to provide a falsely colored oximetry image illustrating measured oximetry values for each pixel.

23. The method of claim 18 further comprising providing a real time image of oxygen saturation values by repeating said interval for a plurality of intervals at a first predetermined frequency, wherein said real time image is cycled at a second frequency, said second frequency measured as an integer fraction of said first frequency.

24. The method of claim 18 further comprising:
sending said electrical signals to a video processor which forms an image from said electrical signals taken from each sensor wherein said image is comprised of a plurality of pixels;
processing and enhancing said signals with a video processor to provide oxygen saturation levels for each said sensor on a pixel by pixel basis; and
displaying the resulting information on a display monitor.

25. The method of claim 24 wherein a subset of filters corresponds to one pixel of information.

26. The method of claim 18 wherein said plurality of light components comprises at least three light components, each said light component comprising a band of light wavelengths; and
wherein the amount of light sensed of each of said at least three light components is used to calculate said oxygen saturation values.

27. The method of claim 26 wherein:
said plurality of light components comprises a first, second and third light component, wherein:
said first light component represents an isobestic point;
said second light component represents a band of wavelengths where the average extinction values for oxyhemoglobin are greater than the average extinction values for reduced hemoglobin; and
said third light component represents a band of wavelengths where the average extinction values for oxyhemoglobin are less than the average extinction values for reduced hemoglobin.

28. The method of claim 27 wherein:
the first light component includes wavelengths of between about 520 nm and 590 nm;
the second light component includes wavelengths of between about 450 nm and 520 nm; and
the third light component includes wavelengths of between about 590 nm and 800 nm.

29. The method of claim 18 wherein said light sensors of each said subset area are arranged in an alternating fashion on the array of filters so that a subset area of filters contains representative information for each of the light components.

30. The method of claim 29 wherein said filter subsets at least partially overlap at least one of other said filter subset.

31. The method of claim 18 further comprising:
reducing the glare of reflected light from the tissue scene by providing a first polarizing filter between the light source and the tissue and a second polarizing filter between said tissue and said array of sensors; wherein said first filter is oriented at a different polarizing angle from the second filter.

* * * * *